(12) United States Patent
Wenchell

(10) Patent No.: US 8,157,830 B2
(45) Date of Patent: Apr. 17, 2012

(54) APPARATUS FOR APPLYING WOUND TREATMENT MATERIAL USING TISSUE-PENETRATING NEEDLES

(75) Inventor: Thomas Wenchell, Durham, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 0 days.

(21) Appl. No.: 12/751,244

(22) Filed: Mar. 31, 2010

(65) Prior Publication Data
US 2010/0204641 A1 Aug. 12, 2010

Related U.S. Application Data

(63) Continuation of application No. 11/250,232, filed on Oct. 14, 2005.

(60) Provisional application No. 60/620,170, filed on Oct. 18, 2004.

(51) Int. Cl.
*A61B 17/34* (2006.01)

(52) U.S. Cl. ......................... 606/186; 606/214

(58) Field of Classification Search .................. 606/214, 606/219, 220, 186; 604/22
See application file for complete search history.

(56) References Cited

U.S. PATENT DOCUMENTS

| | | | |
|---|---|---|---|
| 3,079,606 A | 3/1963 | Bobrov et al. | |
| 3,490,675 A | 1/1970 | Green et al. | |
| 3,499,591 A | 3/1970 | Green | |
| 4,230,001 A * | 10/1980 | Noll et al. | 81/9.22 |
| 4,392,493 A * | 7/1983 | Niemeijer | 606/116 |
| 4,429,695 A | 2/1984 | Green | |
| 4,873,977 A | 10/1989 | Avant et al. | |
| 5,065,929 A | 11/1991 | Schulze et al. | |
| 5,156,613 A | 10/1992 | Sawyer | |
| 5,156,614 A | 10/1992 | Green et al. | |
| 5,254,113 A | 10/1993 | Wilk | |
| 5,318,531 A | 6/1994 | Leone | |
| 5,392,979 A | 2/1995 | Green et al. | |
| 5,465,896 A | 11/1995 | Allen et al. | |
| 5,542,594 A | 8/1996 | McKean et al. | |
| 5,554,119 A | 9/1996 | Harrison et al. | |
| 5,611,775 A | 3/1997 | Machoid et al. | |
| 5,669,934 A | 9/1997 | Sawyer | |
| 5,690,675 A | 11/1997 | Sawyer et al. | |
| 5,749,895 A | 5/1998 | Sawyer et al. | |
| 5,799,857 A | 9/1998 | Robertson et al. | |
| 5,824,015 A | 10/1998 | Sawyer | |
| 5,843,033 A | 12/1998 | Ropiak | |

(Continued)

FOREIGN PATENT DOCUMENTS

EP 0 577 373 1/1994

(Continued)

*Primary Examiner* — Ryan Severson
*Assistant Examiner* — Julie A Szpira

(57) ABSTRACT

A surgical apparatus is provided including a disposable loading unit selectively operatively engagable within a distal end of a first half-section; and a wound treatment material applicator assembly for delivering wound treatment material to the target surgical site. The disposable loading unit includes a cartridge; a plurality of deployable needles supported within the cartridge, wherein each needle includes a lumen extending therethrough and at least one hole formed in an outer periphery thereof; and an actuation member translatably disposed within the cartridge for delivering a driving force to each needle to deploy the needles from the cartridge. The applicator assembly includes a first and second reservoir supported on the distal end of a respective first and second half-section; and a source of wound treatment material in fluid communication with each reservoir.

12 Claims, 7 Drawing Sheets

U.S. PATENT DOCUMENTS

| | | |
|---|---|---|
| 5,866,561 A | 2/1999 | Ungs |
| 5,895,412 A | 4/1999 | Tucker |
| 5,915,616 A | 6/1999 | Viola et al. |
| 5,931,165 A | 8/1999 | Reich et al. |
| 5,948,123 A * | 9/1999 | Hirata et al. ............... 8/404 |
| 5,964,394 A | 10/1999 | Robertson |
| 6,032,849 A | 3/2000 | Mastri et al. |
| 6,045,560 A | 4/2000 | McKean et al. |
| 6,149,641 A | 11/2000 | Ungs |
| 6,165,201 A | 12/2000 | Sawhney et al. |
| 6,179,862 B1 | 1/2001 | Sawhney |
| 6,228,051 B1 | 5/2001 | Trumbull |
| 6,287,323 B1 | 9/2001 | Hammerslag |
| 6,398,797 B2 | 6/2002 | Bombard et al. |
| 6,451,029 B1 | 9/2002 | Yeatman |
| 6,488,197 B1 | 12/2002 | Whitman |
| 6,491,201 B1 | 12/2002 | Whitman |
| 6,588,301 B1 * | 7/2003 | Chanet et al. ............... 81/9.22 |
| 6,623,452 B2 | 9/2003 | Chien et al. |
| 6,629,949 B1 * | 10/2003 | Douglas ............... 604/46 |
| 6,681,979 B2 | 1/2004 | Whitman |
| 6,689,103 B1 * | 2/2004 | Palasis ............... 604/173 |
| 6,695,199 B2 | 2/2004 | Whitman |
| 7,238,195 B2 * | 7/2007 | Viola ............... 606/219 |
| 7,517,356 B2 * | 4/2009 | Heinrich ............... 606/219 |
| 2001/0007069 A1 | 7/2001 | Bombard et al. |
| 2002/0010482 A1 | 1/2002 | Watt |
| 2002/0026159 A1 | 2/2002 | Zhu et al. |
| 2002/0049454 A1 | 4/2002 | Shitman et al. |
| 2002/0156150 A1 | 10/2002 | Williams et al. |
| 2002/0165562 A1 | 11/2002 | Grant et al. |
| 2002/0173558 A1 | 11/2002 | Williams et al. |
| 2003/0050590 A1 | 3/2003 | Kirsch |
| 2003/0073981 A1 | 4/2003 | Whitman et al. |
| 2003/0073982 A1 | 4/2003 | Whitman |
| 2003/0089757 A1 | 5/2003 | Whitman |
| 2003/0111507 A1 | 6/2003 | Nunez |
| 2003/0139771 A1 * | 7/2003 | Fisher et al. ............... 606/213 |
| 2003/0208167 A1 * | 11/2003 | Prausnitz et al. ............... 604/272 |
| 2003/0236518 A1 | 12/2003 | Marchitto et al. |
| 2004/0059283 A1 | 3/2004 | Kirwan et al. |
| 2004/0092960 A1 | 5/2004 | Abrams et al. |
| 2004/0093029 A1 | 5/2004 | Zubik et al. |
| 2005/0038471 A1 | 2/2005 | Chan et al. |
| 2005/0043678 A1 | 2/2005 | Freyman et al. |
| 2005/0184121 A1 | 8/2005 | Heinrich |
| 2006/0235469 A1 * | 10/2006 | Viola ............... 606/219 |
| 2007/0038181 A1 * | 2/2007 | Melamud et al. ............... 604/158 |
| 2007/0118073 A1 * | 5/2007 | Martin et al. ............... 604/46 |

FOREIGN PATENT DOCUMENTS

| | | |
|---|---|---|
| WO | WO 00/56376 | 9/2000 |
| WO | WO 01/62158 | 8/2001 |
| WO | WO 01/62162 | 8/2001 |
| WO | WO 02/30297 | 4/2002 |
| WO | WO 03/088844 | 10/2003 |
| WO | WO 03/094743 | 11/2003 |
| WO | WO 03/094746 | 11/2003 |
| WO | WO 03/105698 | 12/2003 |

\* cited by examiner

APPARATUS FOR APPLYING WOUND TREATMENT MATERIAL USING TISSUE-PENETRATING NEEDLES

CROSS-REFERENCE TO RELATED APPLICATIONS

This application is a continuation of U.S. application Ser. No. 11/250,232 filed Oct. 14, 2005, which claims benefit of application No. 60/620,170 filed Oct. 18, 2004, and the disclosures of each of the above-identified applications are hereby incorporated by reference in their entirety.

BACKGROUND

1. Technical Field

The present disclosure relates to surgical instruments, and more particularly, to a surgical apparatus capable of clamping body tissue and applying a wound treatment material thereto.

2. Description of the Related Art

Surgical procedures requiring cutting of tissue can result in bleeding at the site of the cutting. Various techniques have been developed to successfully control bleeding, such as, for example, suturing, applying clips to blood vessels, and using surgical fasteners, as well as electrocautery and other tissue heating techniques.

Surgical devices using surgical fasteners entail grasping or clamping tissue between opposing jaw structure and then joining the tissue by employing the surgical fasteners. These devices are well known in the art. In some instruments a knife is provided to cut the tissue which has been joined by the fasteners. The fasteners are typically in the form of surgical staples however, two part polymeric fasteners are also utilized.

Instruments for this purpose can comprise two elongated members which are respectively used to capture or clamp tissue. Typically, one of the members carries a cartridge which houses a plurality of fasteners arranged in at least two lateral rows while the other member comprises an anvil which defines a surface for forming the fastener legs as the fasteners are driven from the cartridge. Where two part fasteners are used, the anvil carries the mating part, e.g. the receiver, of the fasteners which are driven from the cartridge. Generally, the stapling operation is effected by a pusher which travels longitudinally through the cartridge carrying member, with the pusher acting upon the staples to sequentially eject them from the cartridge. A knife may travel with the pusher between the staple rows to longitudinally cut (i.e., form a knife cut line) the stapled tissue between the rows of staples. Such instruments are disclosed in U.S. Pat. Nos. 3,079,606 and 3,490,675, the entire contents of each of which are incorporated herein by reference.

A later stapler disclosed in U.S. Pat. No. 3,499,591 provides a double row of staples on each side of the incision or the knife cut line. This is accomplished by providing a cartridge assembly in which a cam member moves through an elongate guide path between two sets of staggered staple carrying grooves. Staple drive members are located within the grooves and are positioned in such a manner so as to be contacted by the longitudinally moving cam to effect ejection of the staples. Other examples of staplers are disclosed in U.S. Pat. Nos. 4,429,695, 5,065,929, and 5,156,614, the entire contents of each of which are incorporated herein by reference.

Electrocautery devices are preferred in certain surgical procedures for effecting improved hemostasis by heating tissue and blood vessels using thermogenic energy, preferably radiofrequency energy, to cause coagulation or cauterization. Monopolar devices utilize one electrode associated with a cutting or cauterizing instrument and a remote return electrode, usually adhered externally to the patient. Bipolar instruments utilize two electrodes and the cauterizing current is generally limited to tissue between the two electrodes of a tissue treating portion (e.g., end effector) of an instrument.

Hemostatic electrosurgical stapling devices combining the structural and functional aspects of stapling instruments and electrocautery devices generally provide improved hemostasis by using thermogenic energy to cause coagulation or cauterization at or in proximity to the knife cut line and surgical fasteners to staple the tissue, either before, during or after the use of thermogenic energy.

Even though stapling, electrocauterizing or a combination of both techniques are generally well suited to control bleeding along the knife cut line, other techniques are envisioned for being used to control bleeding during surgical procedures.

Therefore, it is an aspect of the present disclosure to provide a surgical apparatus for providing hemostasis, tissue joining or welding which does not use conventional techniques.

SUMMARY

The present disclosure relates to surgical apparatus capable of clamping body tissue and applying a wound treatment material thereto.

According to an aspect of the present disclosure, a surgical apparatus is provided including a first half-section adapted to receive a disposable loading unit in a distal end thereof; a second half-section in juxtaposed relation to the first half-section; a disposable loading unit selectively operatively engagable with the distal end of the first half-section; and a wound treatment material applicator assembly for delivering wound treatment material to the target surgical site.

The disposable loading unit includes a cartridge; a plurality of deployable needles supported within the cartridge, wherein each needle includes a lumen extending therethrough and at least one hole formed in an outer periphery thereof; a needle pusher in operative association with each needle for deploying each needle from the cartridge and into a target tissue; and an actuation member translatably disposed within the cartridge for delivering a driving force to each needle pusher to deploy the needles from the cartridge.

The applicator assembly includes a first and second reservoir supported on the distal end of a respective first and second half-section; and a source of wound treatment material in fluid communication with each reservoir.

The source of wound treatment material may include at least one pressurized canister of wound treatment material. Each canister may be supported on one of the first and second half-sections.

Each needle pusher includes an opening formed therein for fluid communication with the lumen of the respective needle.

The distal end of the first half-section includes a plurality of openings provided between the reservoir and the cartridge supported thereon for enabling transmission of wound treatment material from the reservoir to the cartridge. A plate including a plurality of needle receiving openings may be supported on the distal end of the second half-section. Accordingly, a distal end of each needle may enter a respective needle receiving opening of the second half-section during operation of the surgical apparatus.

An elastomeric material may be provided to confine the wound treatment material within the reservoir supported on the distal end of the second half-section. Accordingly, upon actuation of the surgical apparatus, a distal end of each needle penetrates the elastomeric material and the lumen of each needle is in fluid communication with the reservoir supported on the distal end of the second half-section.

The wound treatment material is at least one of an adhesive, a sealant, a hemostat, and a medicament.

The disposable loading unit may include a biasing member operatively associated with at least one of the needles for biasing the needles to a retracted condition. The surgical apparatus may further include a knife blade supported on the actuation sled for severing tissue clamped between the distal ends of the first and second half-sections. The knife blade may travel along a longitudinal slot provided in the cartridge. It is envisioned that at least some needles are disposed on either side of the longitudinal slot of the cartridge.

The applicator assembly may include a valve fluidly interposed between the source of wound treatment material and the reservoir.

According to another aspect of the present disclosure, a method of operating on tissue at a target surgical site is provided. The method includes the step of providing a surgical apparatus. The surgical apparatus includes a disposable loading unit selectively operatively supportable in a distal end of a first half-section, the disposable loading unit having a cartridge operatively supporting a plurality of deployable needles, wherein each needle includes a lumen extending therethrough and at least one hole formed in an outer periphery thereof, and an actuation member translatably disposed within the cartridge for delivering a driving force to each needle to deploy the needles from the cartridge. The surgical apparatus further includes a wound treatment material applicator assembly for delivering wound treatment material to the target surgical site. The applicator assembly includes at least one reservoir supported on a distal end of one of a first and second half-section, and a source of wound treatment material in fluid communication with each reservoir;

The method further includes the steps of clamping adjacent layers of tissue between a distal end of a first and a second half-section of the surgical apparatus; firing the surgical apparatus, wherein firing of the surgical apparatus includes distally advancing the actuation member to drive the plurality of needles through the clamped tissue, and dispensing wound treatment material to the clamped tissue from the source of wound treatment material, through the plurality of needles.

The source of wound treatment material may be pressurized. Accordingly, upon firing the surgical apparatus the wound treatment material is expelled from the source thereof Additionally, upon firing of the surgical apparatus a distal end of each needle desirably enters a distal end of the second half-section.

The surgical apparatus may include a reservoir supported on a distal end of each of the first and second half-sections. Accordingly, the wound treatment material may be delivered to the lumen of each needle from each of the reservoirs.

The surgical apparatus may further include a knife blade translatably movable along the distal ends of the first and second half-sections to sever tissue clamped therebetween, wherein upon firing the surgical apparatus the knife blade is distally advanced along the distal ends of the first and second half-sections to sever the tissue clamped therebetween.

BRIEF DESCRIPTION OF THE DRAWINGS

Various embodiments of the surgical apparatus will be described hereinbelow with reference to the drawings wherein.

DETAILED DESCRIPTION OF EMBODIMENTS

Figure 1:
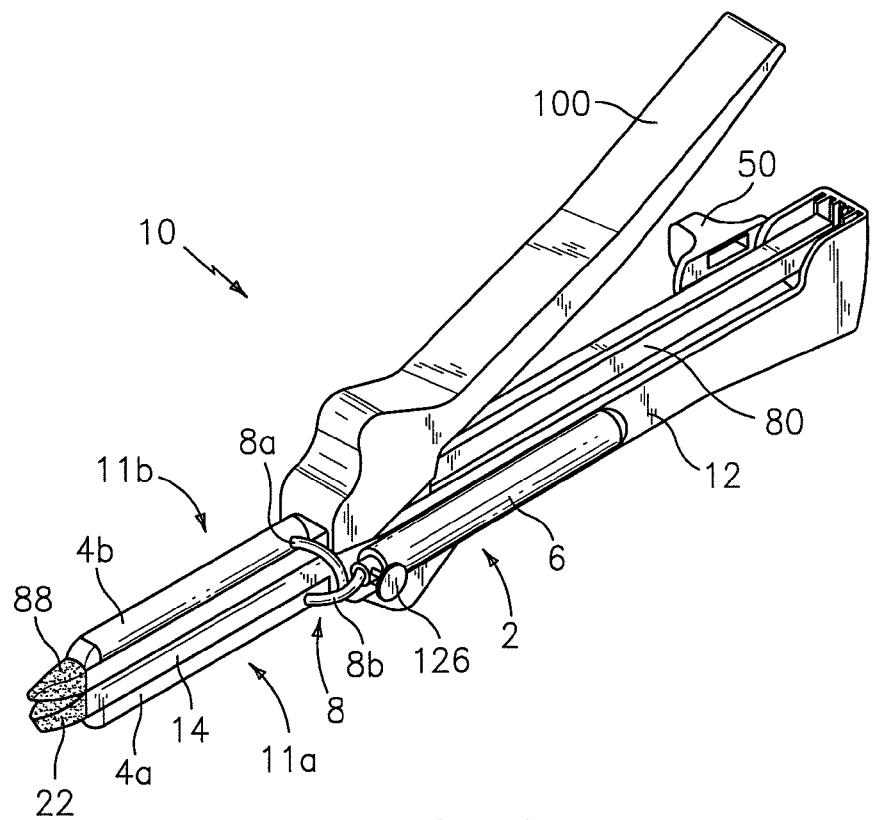
FIG. 1 is a perspective view of a surgical apparatus having a wound treatment material applicator constructed in accordance with a preferred embodiment with the clamping handle thereof disposed in an upright open position.

The present disclosure provides a surgical apparatus which uses biological and/or synthetic biocompatible sealants, hemostats and adhesives (collectively referred to herein as wound treatment materials) for providing hemostasis, tissue joining or welding. The use of wound treatment materials provides short and long-term hemostasis and sealing, and/or reduces or prevents bleeding along a knife cut line.

In the drawings and in the following description, the term "proximal", as is traditional, will refer to the end of the apparatus which is closer to the operator, while the term "distal" will refer to the end of the apparatus which is further from the operator.

Figure 2:
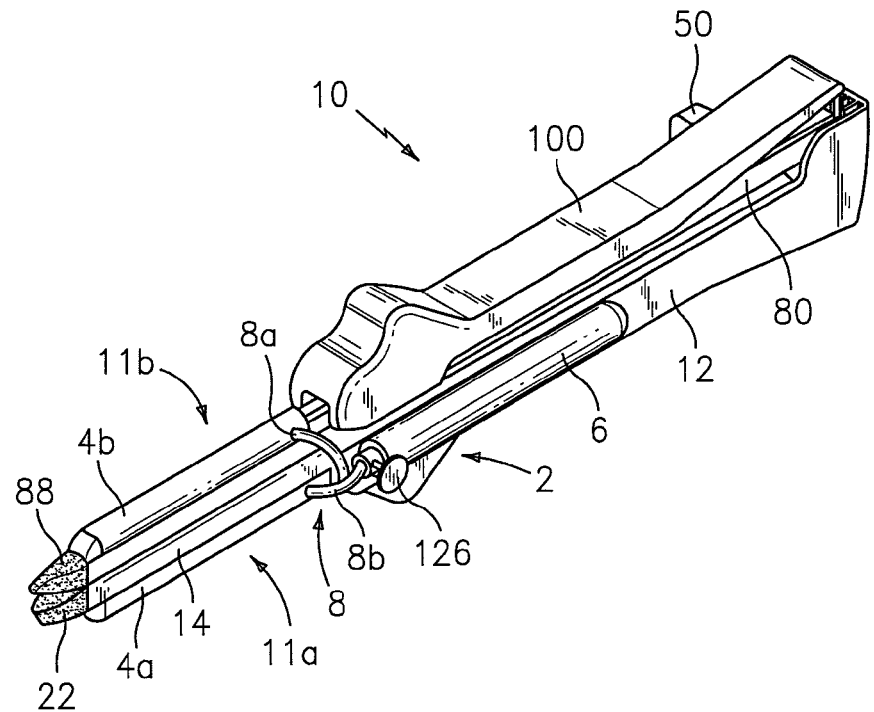
FIG. 2 is a perspective view of the surgical apparatus illustrated in FIG. 1 with the clamping handle disposed in a closed position.

Referring now to the drawings wherein like reference numerals identify similar structural elements, there is illustrated in FIGS. 1 and 2 a surgical apparatus 10, having a wound treatment material applicator constructed in accordance with a preferred embodiment, is illustrated. Surgical apparatus 10 includes a cartridge or needle-releasing half-section 11*a* (hereinafter referred to as first half-section) and an anvil or needle-receiving half-section 11*b* (hereinafter referred to as second half-section). As will become readily apparent to those having ordinary skill in the art, apparatus 10 is constructed in such a manner so as to substantially reduce the costs associated with its fabrication and assembly.

Figure 3:
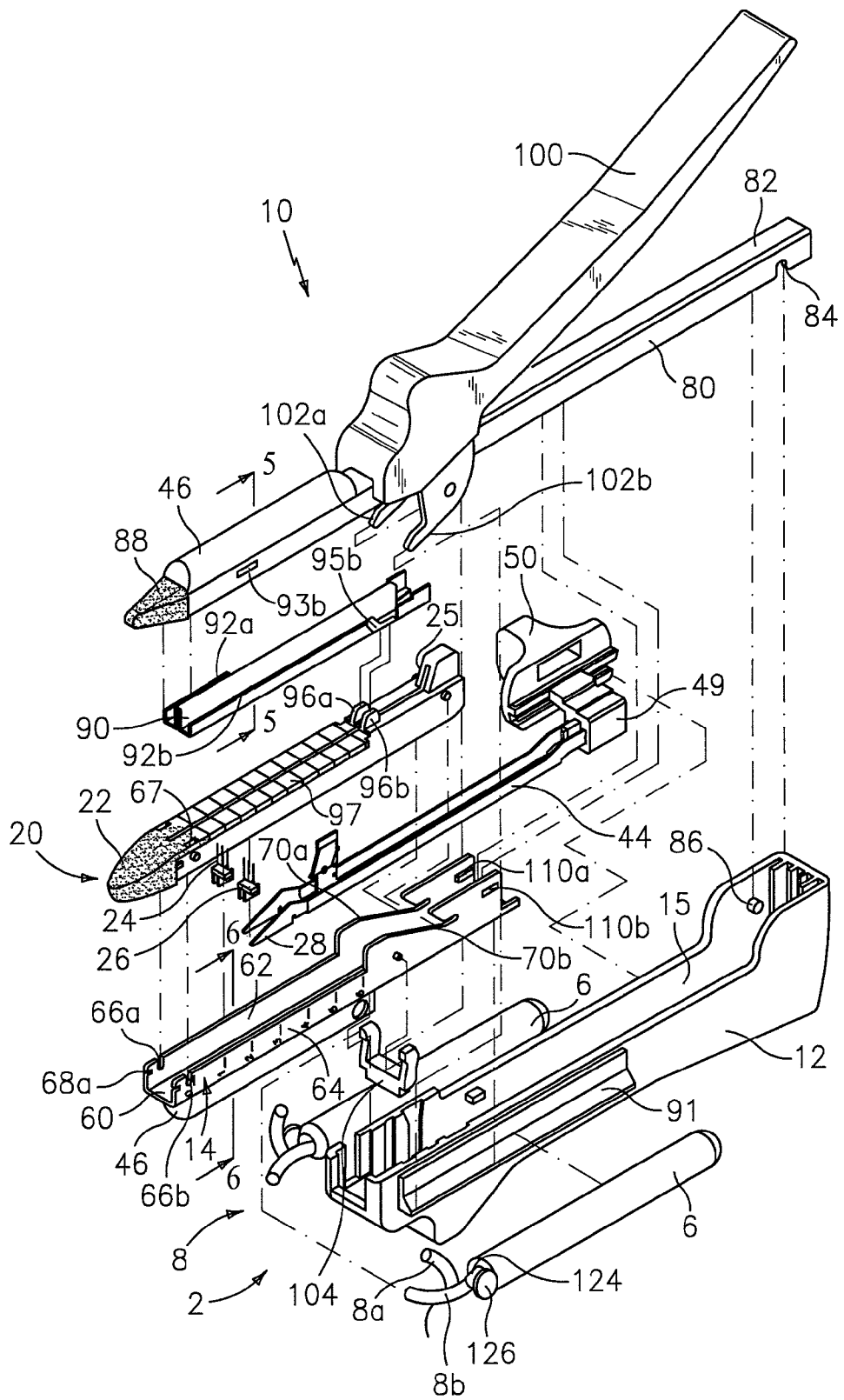
FIG. 3 is an exploded perspective view of the surgical apparatus of FIGS. 1 and 2.

Referring to FIGS. 1-3, integral with first half-section 11*a*, apparatus 10 includes a body portion 12 defining a handle for grasping and supporting the device. A retaining channel 14 is mounted in the interior cavity 15 of body portion 12 adjacent the distal end thereof. Retaining channel 14 is dimensioned and configured to support a disposable loading unit 20.

Figure 4:
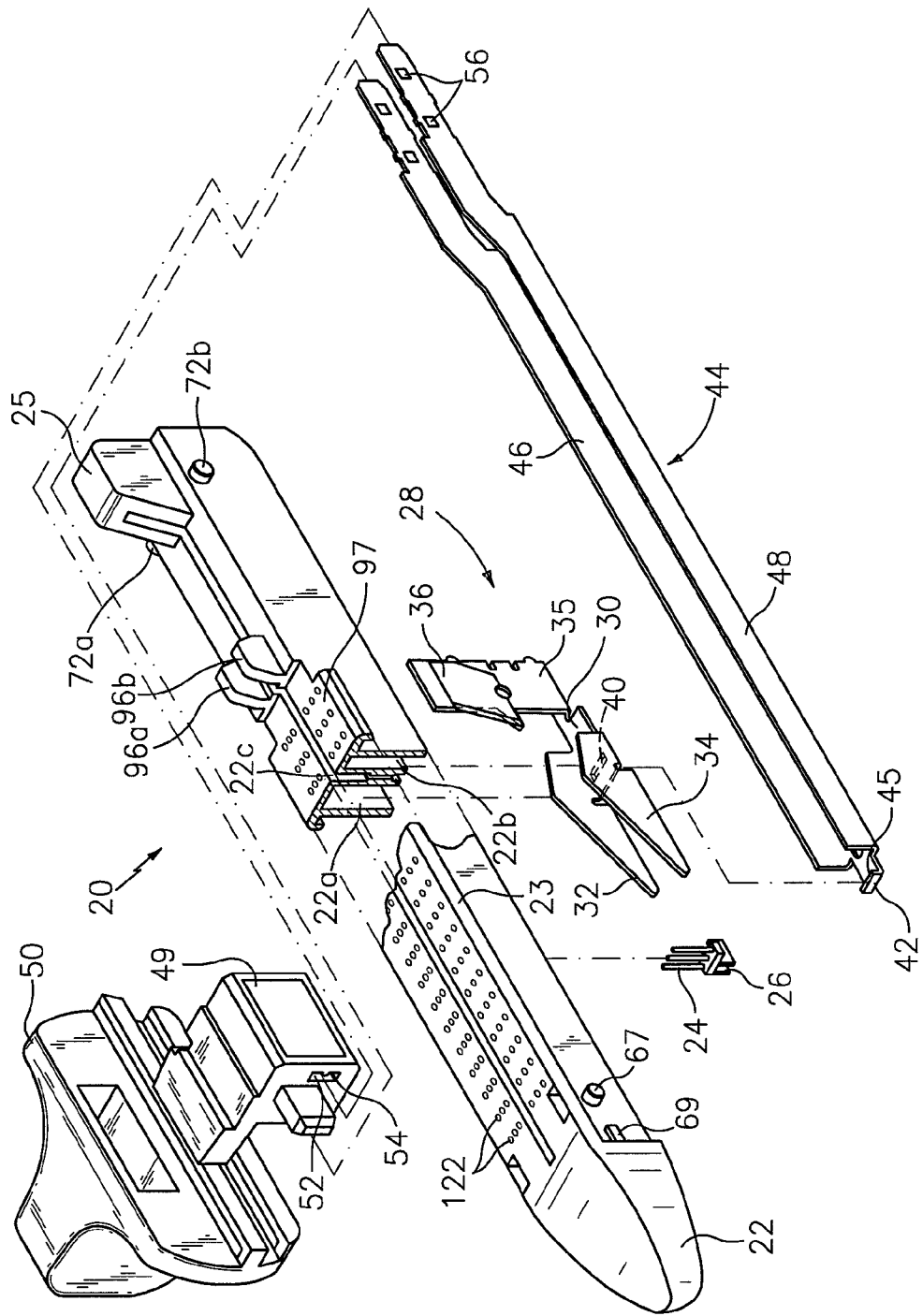
FIG. 4 is an exploded perspective view of the lower body portion of the surgical apparatus of FIGS. 1 and 2.
Figure 7:
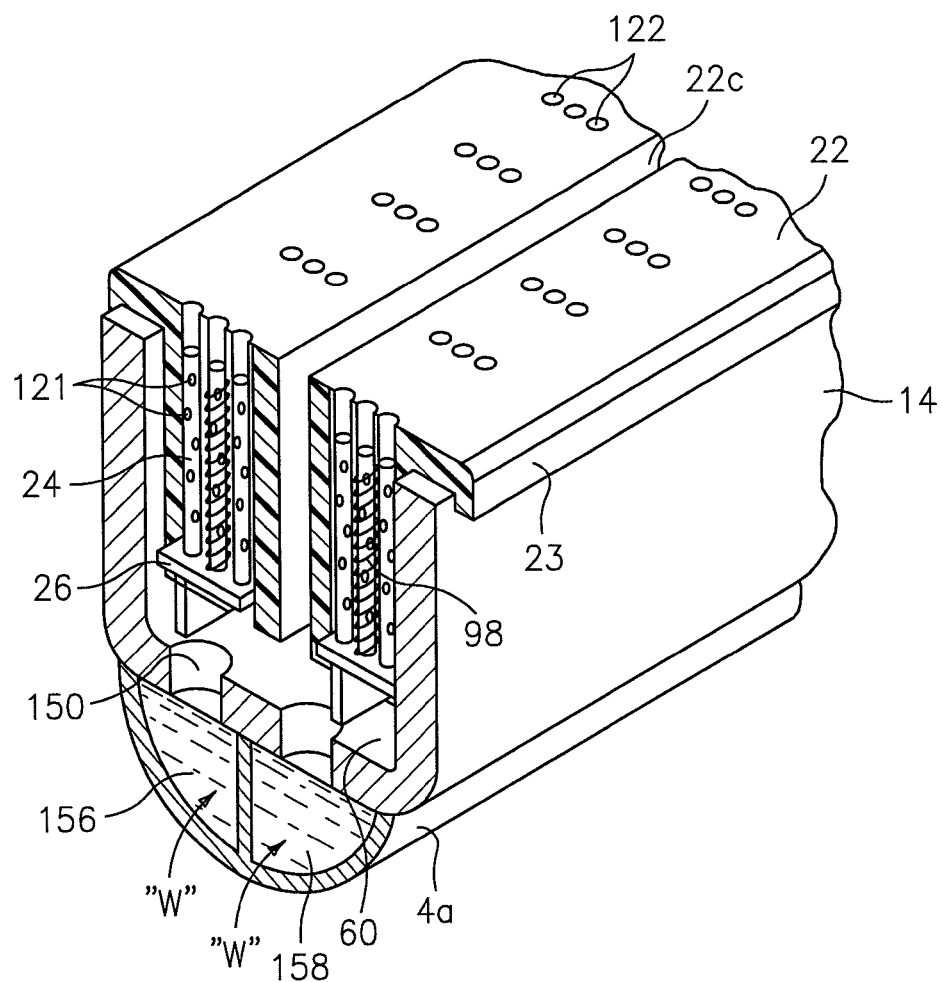
FIG. 7 is an enlarged perspective and partial vertical cross-sectional view with parts broken away of a portion of the adhesive applicator of the surgical apparatus of FIGS. 1 and 2.
Figure 8:
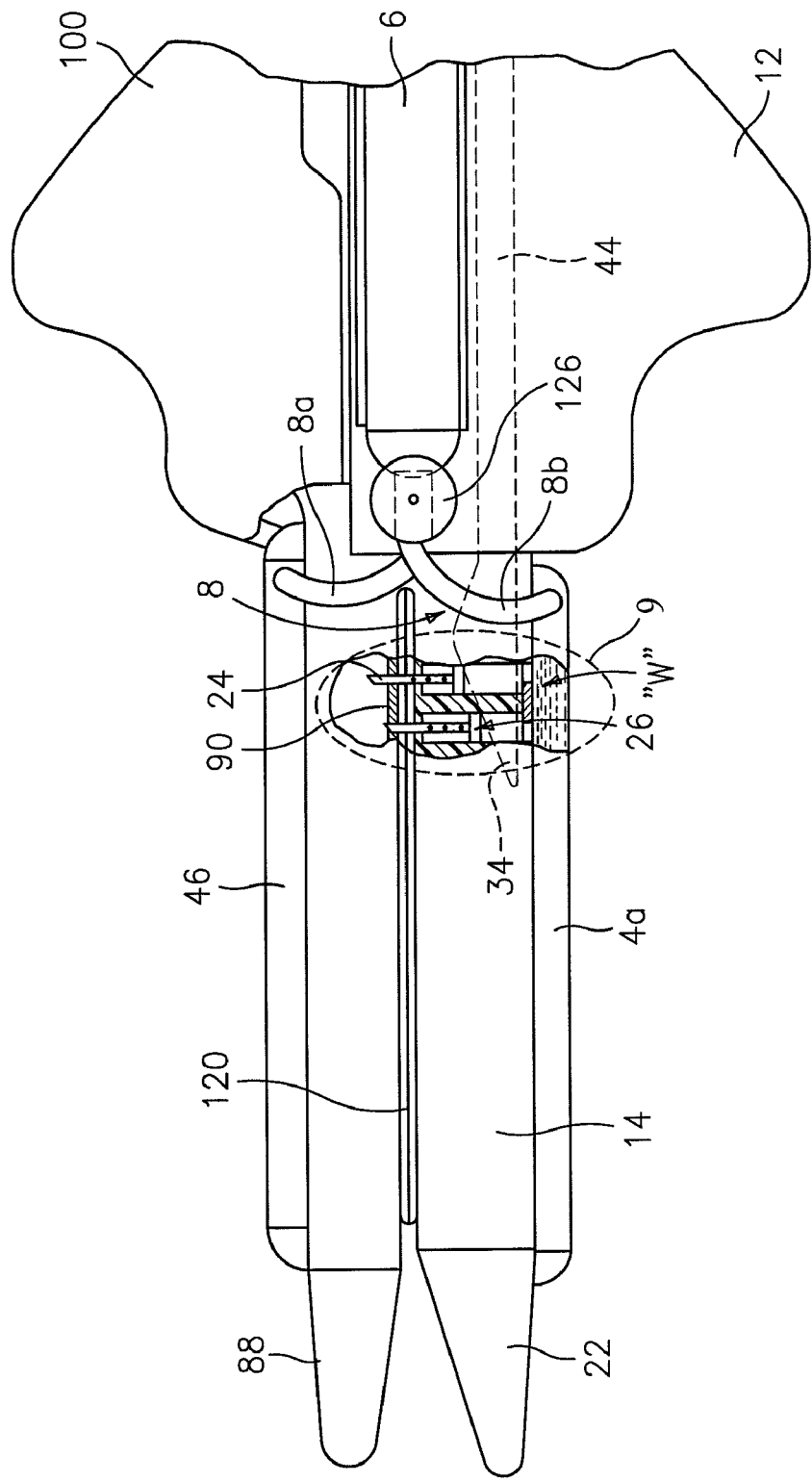
FIG. 8 is an enlarged side view with portions broken away showing the surgical apparatus of FIGS. 1 and 2 clamping and applying adhesive to body tissue.
Figure 9:
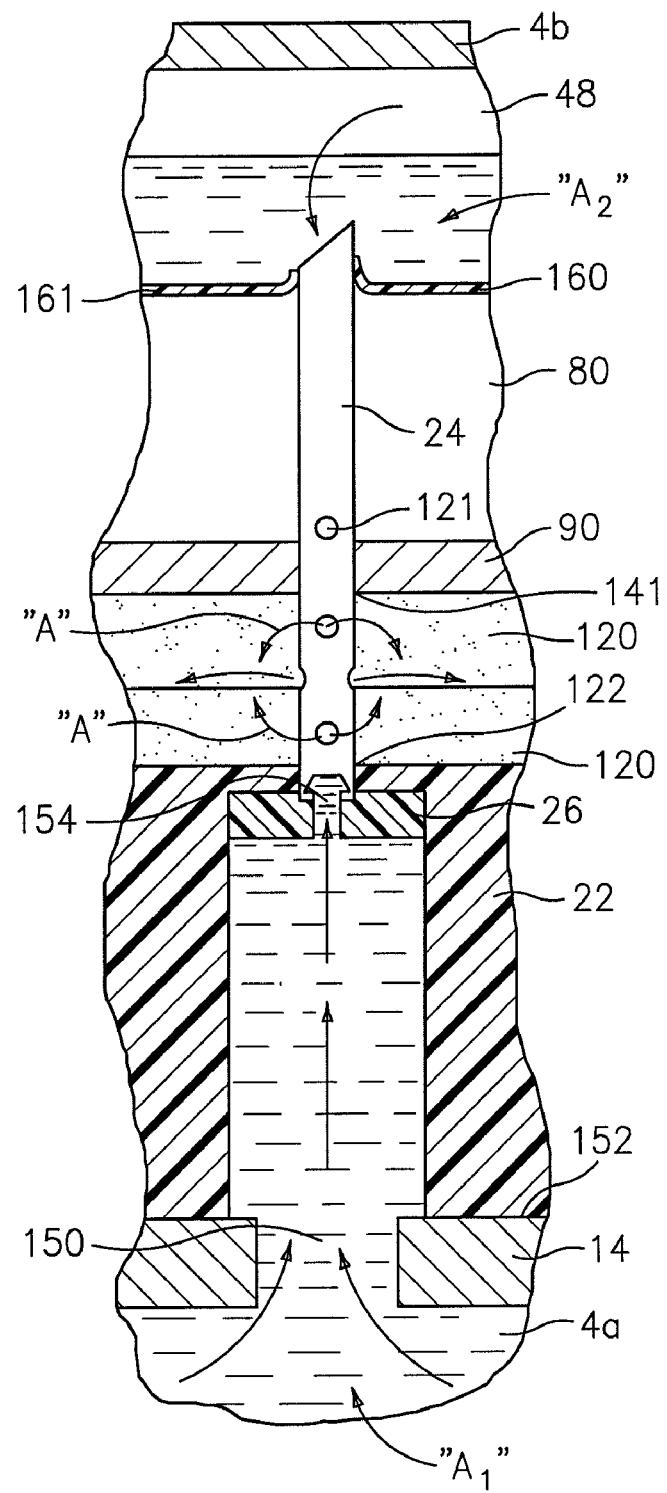
FIG. 9 is an enlarged sectional view of a portion of the wound treatment material applicator as would be seen along line 9-9 of FIG. 8 showing application of wound treatment material by the wound treatment material applicator to adjoin body tissue.

As shown in FIGS. 4, 7 and 9, disposable loading unit 20 includes a cartridge 22 having a plurality of slots 22a, 22b which retain a plurality of surgical needles 24. The disposable loading unit 20 further includes a plurality of needle pushers 26 adapted and configured to push or deploy needles 24 outside of or out through the slots 22a, 22b when acted upon by a driving force. Needle pushers 26 are also configured and dimensioned to feed wound treatment material "W" into the interior of needles 24 via central openings 154 formed in pushers 26 (see FIG. 9). The disposable loading unit 20 further includes an actuation member 28 (FIGS. 3, 4 and 8), here shown, for example, as a sled, mounted to translate through cartridge 22 in a longitudinal direction to transmit a driving force to pushers 26 for applying or dispensing wound treatment material "W" to a surgical application site from or through holes 121 on the periphery of the needles 24 (see FIG. 9). While actuation member 28 is shown as a sled, it is envisioned and within the scope of the present disclosure for actuation member 28 to be cam rollers, cam slides and the like, as will be described in greater detail below with reference to FIG. 10.

Referring back to FIGS. 1-3, wound treatment material "W", or a component thereof, is supplied to the surgical application site by an applicator assembly 2. Applicator assembly 2 includes a pair of reservoirs 4a, 4b in fluid communication with respective distal ends of first and second half-sections 11a, and 11b. Reservoirs 4a, 4b are in fluid communication with pressure-actuating fluid (gas or liquid) canisters 6, via conduit assemblies 8. Preferably, the fluid is a gas. An upper and a lower conduit 8a, 8b, respectively, (see FIGS. 2 and 3) of conduit assembly 8, extend from canister 6, and feed into a respective reservoir 4a, 4b of applicator assembly 2 for delivering pressurized fluid thereto. Each canister 6 is releasably mounted to a respective mounting member or track 91 that is part of or affixed to body portion 12. Each canister 6 includes a nozzle 124 (see FIG. 3) having a valve 126 for controlling the flow of pressurized fluid contained therein to reservoirs 4a, 4b via conduit assemblies 8. The release of the pressurized fluid, from canisters 6, forces wound treatment material "W" through needles 24 during a surgical wound treatment material applying operation.

Figure 6:
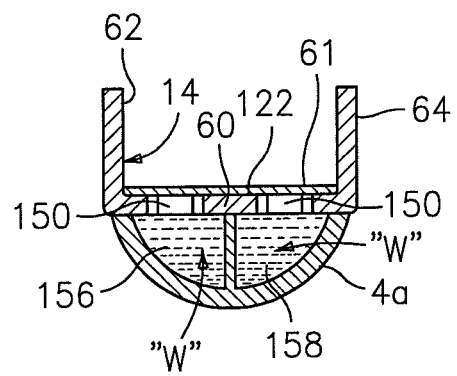
FIG. 6 is a cross-sectional view of cartridge components construed, and as would be seen along line 6-6 in FIG. 3.

In order to provide wound treatment material "W" from reservoir 4a to the interior of retaining channel 14, as seen in FIGS. 6 and 7, retaining channel 14 includes, preferably initially sealed, openings 150 formed along a base portion 60 thereof for passage of wound treatment material "W" from reservoir 4a mounted below retaining channel 14. In use, in accordance with a method of the present disclosure, after removal, breakage, penetration or otherwise providing access or passage through a seal 61 (see FIG. 6) overlying base portion 60, wound treatment material "W" flows from reservoir 4a into the interior of retaining channel 14, through openings 150 due to the pressure provided by the pressurized fluid of canisters 6, and finally into and through the interior of needles 24 before being dispensed with, onto, above, below and/or between layers of tissue 120 (see FIG. 9).

In a preferred embodiment, one of reservoirs 4a, 4b stores one component of a wound treatment material "W" used in forming a two-part adhesive, e.g., a glue, while the other of reservoirs 4a, 4b stores a second component of the wound treatment material "W" used in forming the two-part adhesive, e.g., an accelerator. In another preferred embodiment, as seen in FIG. 6, a first compartment 156 of each reservoir 4a and/or 4b stores one component of a wound treatment material for forming an adhesive while a second compartment of each reservoir 4a and/or 4b stores a second component of the wound treatment material used in forming the adhesive. Preferably, the first and second components are fed to a common needle for application/delivery of the combined components to or at the treatment site.

Preferably, reservoirs 4a, 4b are identical and encase an equal, complimentary or suitable volumetric amount of respective components of wound treatment material "W" to obtain and/or maintain a predetermined ratio of the first component to the second component, which ratio may be 1:1. Also, preferably, the adhesive formed by the two components of wound treatment material "W" is fibrin glue or fibrin sealant which acts as a hemostatic agent and as a tissue adhesive.

Fibrin sealant is formed by a rapid polymerization which occurs when a solution of proteomic clotting factors, such as fibrinogen, comes into contact with a solution of a proteomic catalyst, such as thrombin. This rapid polymerization typically commences within two seconds after the solutions initially contact one another, and it typically attains a soft set within ten seconds of contact. Because of the rapid polymerization upon intimate interaction of fibrinogen and thrombin, it is important to maintain these two blood proteins separate until applied at the application site. Accordingly, it is preferred that applicator assembly 2 supplies each blood protein separately from the other blood protein by using a separate conduit assembly for each protein and by compartmentalizing surgical needles 24 to prevent mixing of the two components prior to being applied to the application site.

It is contemplated that the wound treatment material "W" is any material for joining, healing, sealing or otherwise treating tissue. In a preferred embodiment, the wound treatment material is a bio-compatible sealant, including, and not limited to, sealants which cure upon tissue contact, sealants which cure upon exposure to ultraviolet (UV) light, sealants which are two-part systems which are kept isolated from one another and are combined or any combinations thereof Any known suitable adhesive may be used. In one embodiment, it is contemplated that such sealants and/or adhesives are curable. For example, sealants may have a cure time of from about 10 to 15 seconds may be used. In preferred embodiments, the sealant and/or adhesive is a bioabsorbable and/or bio-resorbable material. In another embodiment, it is contemplated that a sealant and/or adhesive having a cure time of about 30 seconds may be used. It is further envisioned that wound treatment material "W" may be a pre-cured adhesive or sealant. The pre-cured adhesive or sealant may react with the moisture and/or heat of the body tissue to thereby activate the sealing and/or adhesive properties of the sealant or adhesive.

In certain preferred embodiments, the wound treatment material comprises a sealant. Such a sealant is desirably a PEG-based material. Examples of classes of materials useful as the sealant and/or adhesive include acrylate or methacrylate functional hydrogels in the presence of a biocompatible photoinitiator, alkyl-cyanoacrylates, isocyanate functional macromers with or without amine functional macromers, succinimidyl ester functional macromers with amine or sulfhydryl functional macromers, epoxy functional macromers with amine functional macromers, mixtures of proteins or polypeptides in the presence of aldehyde crosslinkers, Genipin, or water-soluble carbodiimides, anionic polysaccharides in the presence of polyvalent cations, etc.

Some specific materials which may be utilized include isocyanate terminated hydrophilic urethane prepolymers derived from organic polyisocyanates and oxyethylene-based diols or polyols, including those disclosed in U.S. Pat. Nos. 6,702,731 and 6,296,607 and U.S. Published Patent Application No. 2004/0068078; alpha-cyanoacrylate based adhesives including those disclosed in U.S. Pat. No. 6,565,840; alkyl ester based cyanoacrylate adhesives including those disclosed in U.S. Pat. No. 6,620,846; adhesives based on biocompatible cross-linked polymers formed from water soluble precursors having electrophilic and nucleophilic groups capable of reacting and cross-linking in situ, including those disclosed in U.S. Pat. No. 6,566,406; two part adhesive systems including those based upon polyalkylene oxide backbones substituted with one or more isocyanate groups in combination with bioabsorbable diamine compounds, or polyalkylene oxide backbones substituted with one or more amine groups in combination with bioabsorbable diisocyanate compounds as disclosed in U.S. Published Patent Application No. 2003/0032734, the contents of which are incorporated by reference herein; and isocyanate terminated hydrophilic urethane prepolymers derived from aromatic diisocyanates and polyols as disclosed in U.S. Published Patent Application No. 2004/0115229, the contents of which are incorporated by reference herein.

It is envisioned and within the scope of the present disclosure that wound treatment material "W" may include one or a combination of adhesives, hemostats, sealants, or any other tissue or wound-treating material. Surgical biocompatible wound treatment materials "W", which may be used in accordance with the present disclosure, include adhesives whose function is to attach or hold organs, tissues or structures, sealants to prevent fluid leakage, and hemostats to halt or prevent bleeding. Examples of adhesives which can be employed include protein derived, aldehyde-based adhesive materials, for example, the commercially available albumin/glutaraldehyde materials sold under the trade designation BioGlue™ by Cryolife, Inc., and cyanoacrylate-based materials sold under the trade designations Indermil™ and Derma Bond™ by Tyco Healthcare Group, LP and Ethicon Endosurgery, Inc., respectively. Examples of sealants, which can be employed, include fibrin sealants and collagen-based and synthetic polymer-based tissue sealants. Examples of commercially available sealants are synthetic polyethylene glycol-based, hydrogel materials sold under the trade designation CoSeal™ by Cohesion Technologies and Baxter International, Inc. Examples of hemostat materials, which can be employed, include fibrin-based, collagen-based, oxidized regenerated cellulose-based and gelatin-based topical hemostats. Examples of commercially available hemostat materials are fibrinogen-thrombin combination materials sold under the trade designations CoStasis™ by Tyco Healthcare Group, LP, and Tisseel™ sold by Baxter International, Inc. Hemostats herein include astringents, e.g., aluminum sulfate, and coagulants.

The medicament may include one or more medically and/or surgically useful substances such as drugs, enzymes, growth factors, peptides, proteins, dyes, diagnostic agents or hemostasis agents, monoclonal antibodies, or any other pharmaceutical used in the prevention of stenosis.

Wound treatment material "W" may include visco-elastic film forming materials, cross-linking reactive agents, and energy curable adhesives. It is envisioned that wound treatment material "W", and in particular, adhesive may be cured with the application of water and/or glycerin thereto. In this manner, the water and/or glycerin cure the adhesive and hydrate the wound.

It is envisioned that wound treatment material "W" may be a relatively low viscosity fluid or liquid such that the wound treatment material "W" may freely flow through conduits 8 and/or needles 24. It is further envisioned that wound treatment material "W" may include a fine powder of particulate material.

It is further contemplated that wound treatment material "W" may include, for example, compositions and/or compounds which accelerate or beneficially modify the healing process when particles of the composition and/or compound are applied to or exposed to a surgical repair site. For example, the wound treatment material "W" may be a therapeutic agent which will be deposited at the repair site. The therapeutic agent can be chosen for its antimicrobial properties, capability for promoting repair or reconstruction and/or new tissue growth Antimicrobial agents such as broad spectrum antibiotic (gentamycin sulfate, erythromycin or derivatized glycopeptides) which are slowly released into the tissue can be applied in this manner to aid in combating clinical and sub-clinical infections in a tissue repair site. To promote repair and/or tissue growth, wound treatment material "W" may include one or several growth promoting factors, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dismutase to scavenge tissue damaging free radicals, tumor necrosis factor for cancer therapy or colony stimulating factor and interferon, interleukin-2 or other lymphokine to enhance the immune system.

Cartridge 22 is preferably fabricated from a liquid crystal polymer material, although other materials are contemplated. Cartridge 22 has a lip 23 which engages the retention channel 14 to secure, stabilize and, e.g., prevent inward rotation of cartridge 22.

As seen in FIGS. 3 and 4, for simplicity and ease of manufacturing and assembly, actuation sled 28 is preferably monolithically formed from a single piece of sheet metal which is folded into the desired structural configuration. In this configuration, actuation sled 28 defines a base portion 30, two upstanding cam wedges 32 and 34, and an upstanding shank 35 which supports a knife blade 36. Knife blade 36 is preferably spot welded to shank 35, although other known fastening methods may be employed.

Cam wedges 32 and 34 are axially staggered with respect to one another so that one leads the other throughout the sled's translation through cartridge 22. In doing so, the driving forces within cartridge 22 remain balanced during a surgical driving operation. Longitudinal slots 22a and 22b accommodate the longitudinal translation of cam wedges 32 and 34, while slot 22c accommodates the longitudinal translation of shank 35.

The base portion of actuation sled 28 has a transverse slot 40 defined therein which is dimensioned and configured to releasably retain an upturned flange 42 formed at the distal end of elongated actuation channel 44 (see FIG. 4). When the disposable loading unit 20 is placed into retaining channel 14 and actuation sled 28 is disposed in its proximal-most position, flange 42 releasably engages slot 40. Thus, movement of actuation channel 44 moves actuation sled 28 which, in turn, engages pushers 26 to deploy needles 24. After an adhesive application operation, disposable loading unit 20 can be removed from the retaining channel by easily disengaging flange 42 from slot 40.

With continued reference to FIG. 4, actuation channel 44 is defined by a base portion 45 and two parallel upstanding beams 46 and 48 of elongate configuration. The distal ends of beams 46 and 48 are staggered to match the staggered orientation of cam wedges 32 and 34, respectively. The proximal end of each beam 46, 48 projects rearwardly to engage a mounting block 49 that is associated with a firing knob 50. A pair of slots 52 (only one of which is shown) are formed in mounting block 49 for receiving the proximal end of each of the upstanding beams 46, 48 of actuation channel 44. Slots 52 are provided with detents 54 for engaging apertures 56 in the beam ends to lockingly retain beams 46, 48 in mounting block 49. In use, longitudinal movement of firing knob 50 causes corresponding longitudinal translation of actuation channel 44 and actuation of sled 28.

Referring to FIGS. 3 and 6, retention channel 14 includes a base portion 60 and two upstanding parallel walls 62 and 64. Numerical indicia are imprinted on the walls 62, 64 of retention channel 14 to indicate the length of the adhesive line. Retention structures are provided at the distal end of each of the walls 62, 64 to engage corresponding structures provided on the disposable loading unit 20. In particular, notches 66a and 66b are provided for engaging corresponding protuberances, such as protuberance 67, and slots 68a and 68b are provided for engaging corresponding detents, such as detent 69. These structures inhibit lateral, longitudinal and perpendicular shifting of the cartridge 22 (and disposable loading unit 20) within the retaining channel 14. Ramped engagement slots 70a and 70b are also defined in the opposed walls of retention channel 14 for interacting with a pair of opposed protuberances 72a and 72b (see FIGS. 3 and 4) to guide the disposable loading unit 20 into retention channel 14 when loaded into the surgical apparatus 10.

With continued reference to FIG. 3, surgical apparatus 10 further includes an elongate anvil support beam 80 which has a generally U-shaped cross-sectional configuration. Proximal end portion 82 of support beam 80 has a notched area 84 for engaging a pair of corresponding detents 86 (only one being shown) which extend into the cavity 15 of body portion 12 adjacent the proximal end thereof. Detents 86 are engaged when cartridge or first half-section 11a and anvil or second half-section 11b is mated with one another. Distal end portion 88 of anvil support beam 80 is configured to support a preformed plate 90 having a plurality of openings 141 (see FIG. 9) in juxtaposed alignment with a respective needle 24 for receiving a portion of the needle 24 therein during the surgical procedure.

Figure 5:
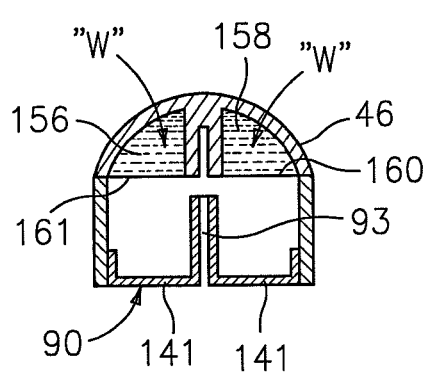
FIG. 5 is a cross-sectional view of the anvil components as would be seen along line 5-5 in FIG. 3.

Plate 90 is preferably formed from a unitary piece of metal and is cold formed and stamped to define the plurality of needle receiving openings 141 (see FIG. 5). Each needle receiving opening 141 is in alignment with a particular needle 24 housed within cartridge 22. Plate 90, as shown in FIG. 3, is provided with two opposed tangs 92a and 92b which extend inwardly to engage complementary engagement slots 93b (only one being shown) in anvil support beam 80 during fabrication and assembly. The cross-sectional configuration of plate 90 is dimensioned to complement the cross-sectional geometry of support beam 80 (see FIG. 5). More particularly, cavity 93 which extends along the length of plate 90 corresponds to a similar channel formed in support beam 80. These areas accommodate shank 35 and knife blade 36 as it translates distally to form an incision in the body tissue, which incision is adjoined by adhesives during a surgical adhesive-applying operation.

A pair of rectangular apertures 95a and 95b are formed in plate 90 adjacent the proximal end thereof for receiving a pair of correspondingly positioned flanges or projections 96a and 96b which project upwardly away from tissue contacting surface 97 (see FIGS. 3 and 4). The interaction between apertures 95a, 95b and flanges 96a, 96b ensures that cartridge 22 and plate 90 are properly aligned with one another during a surgical adhesive-applying procedure.

A bottom surface 160 of the top reservoir 4b preferably is fabricated from an elastomeric or other suitable material 161.

Bottom surface 160 is attached to anvil support beam 80. During a surgical adhesive-applying procedure, needles 24 penetrate elastomeric material 161 of reservoir 4b and pressurized adhesive flows into the interior of needles 24 (see FIG. 9). It is envisioned that elastomeric material 161 can include a series of weakened lines formed therein and in registration with needles 24. In this manner, a reduced force is required for needles 24 to penetrate elastomeric material 161.

After needles 24 dispense wound treatment material "W", needles 24 are retracted into disposable loading unit 20 and elastomeric material 161 reseals reservoir 4b to free tissue 120, 122 from needles 24 and to prevent spillage of the remaining adhesive contained in reservoir 4b. In one embodiment, needles 24 can exit reservoir 4b by the surgeon increasing pressure from reservoir 4b to force needles 24 back into disposable loading unit 20. In another embodiment, a spring 98 (see FIG. 7) can be suitably disposed and/or suitably positioned about each needle 24 to return the needles 24 to the undeployed condition upon retraction of actuation sled 28. In particular, in use, when actuation sled 28 is advanced to displace pushers 26, the springs 98 are compressed and maintained compressed by beams 46, 48 of actuation channel 44 remaining in contact with pushers 26. When actuation sled 28 is withdrawn proximally, after the application of wound treatment material "W", springs 98 expand and thereby move or retract needles 24 back into disposable loading unit 20.

Referring to FIGS. 1-3, anvil or second half-section 11b of apparatus 10 further includes clamping handle 100 which is used to securely clamp tissue between the surface of plate 90 and tissue contacting surface 97 of cartridge 22. Clamping handle 100 is pivotably mounted to anvil support beam 80 about a transverse pivot pin (not shown). A pair of clamping hooks 102a and 102b depend from clamping handle 100 for interacting with U-shaped clamping beam 104 supported within the internal cavity defined in body portion 12.

When apparatus 10 is assembled prior to use, notched area 84 at proximal end 82 of anvil support beam 80 is engaged with the cooperating detents 86 in the inner cavity 15 of body portion 12. Thereupon, anvil or second half-section 11b is mated with cartridge or first half-section 11a, and clamping handle 100 is disposed in the upright unclamped position shown in FIG. 1. Subsequently, when body tissue is properly disposed between the surface of plate 90 and tissue contacting surface 97 of cartridge 22, anvil or second half-section 11b is pivoted towards cartridge or first half-section 11a, about the detents in body portion 12, such that the distal ends of clamping hooks 102a and 102b are positioned immediately adjacent the proximal end of the base of U-shaped clamping beam 104. Concomitantly, flanges 96a and 96b engage apertures 95a and 95b in plate 90 to ensure proper alignment of the anvil and the cartridge.

Then, to securely clamp the captured body tissue, clamping handle 100 is pivoted from the position illustrated in FIG. 1 to that which is shown in FIG. 2. At such a time, clamping hooks 102a and 102b engage the base of clamping beam 104, locking the apparatus 10 in a clamped condition. During clamping, the captured body tissue exerts a counter-force against tissue contacting surface 97 of cartridge 22 and the fastener forming surface of the plate 90, urging the two structures apart. To overcome these forces and prevent the proximal portion 82 of anvil support beam 80 from bending, bearing surfaces are defined within retention channel 14 to support the compressive forces generated during clamping. In particular, as illustrated in FIG. 3, opposed bearing shelves 110a and 110b are stamp formed in opposed walls 62 and 64 of retention channel 14. The bearing shelves 110a, 110b are positioned to abut the medial section of anvil support beam 80 proximate the clamping handle pivot point. It is desirable to provide a locking mechanism to prevent reactuation of the apparatus after it has been actuated.

Referring now to FIGS. 7-9, there is illustrated, a method of applying a surgical wound treatment material "W", here an adhesive. According to the procedure a plurality of needles 24 are deployed or pushed from cartridge 22, by actuation sled 28 or by cam wedges or surfaces 32a, 34a (see FIG. 4), through needle exit holes 122 and are driven into tissue 120 before, during or after being received by the needle-receiving openings 141 of plate 90. Meanwhile, knife blade 36 (see FIG. 4) cuts through tissue 120 forming a knife cut line along slot 22c. In operation, prior to firing surgical apparatus 10, actuation sled 28 is in the proximal-most position. At such a time, knife blade 36 is enclosed in protective housing 25 (see FIGS. 3 and 4) formed adjacent the proximal end of disposable loading unit 20.

In order to fire surgical apparatus 10, after tissue 120 has been clamped between the distal ends of first and second half-sections, firing knob 50 is moved in a distal direction. Accordingly, as illustrated in FIG. 8, upon moving firing knob 50 in a distal direction, actuation channel 44 drives actuation sled 28 distally into and through cartridge 22. During its distal translation, the angled leading surfaces of cam wedges 32 and 34 sequentially contact pushers 26, urging them in a direction transverse to the direction of movement of actuation sled 28. As a result, pushers 26 push needles 24 from their individual exit holes 122, driving needles 24 into tissue 120 before being received by corresponding needle-receiving openings 141 provided in plate 90 (see FIG. 9).

Sequential firing of needles 24 continues until actuation sled 28 is advanced to the distal-most end of cartridge 22, at which time, all of the needles 24, once housed within cartridge 22, have been pushed out of disposable loading unit 20 and a knife cut line has been formed in tissue 120 by knife blade 36. The knife cut line and exterior, interior and/or interstitial regions of tissue 120, as desired, are supplied with adhesive by opening valve 126 and allowing pressurized fluid contained in each canister 6 to be released into reservoirs 4a, 4b to thereby force wound treatment material "W", here shown for example as adhesive "A", or each component of adhesive "$A_1$, $A_2$", into the region(s) between tissue 120, through needles 24 and through holes 121 as well as to the knife cut line through slot 22c. Valve 126 is maintained open until either sufficient adhesive "A" is dispensed, the entire adhesive "A" is dispensed, and/or all of the pressure within canister 6 is depleted.

Thereafter, firing knob 50 is retracted to its original position, causing needles 24 to be retracted into disposable loading unit 20, e.g., by way of a compression spring or other biasing means 98 disposed between needle pushers 26 and an inner surface of tissue contacting surface 97 of disposable loading unit 20, the first and second half-sections are separated, and disposable loading unit 20, as well as one or both reservoirs 4a, 4b, may be removed from retaining channel 14. Preferably, biasing means 98 are disposed about each needle 24 of each pusher 26. Subsequently, a new, fully loaded disposable loading unit 20 can be positioned in retaining channel 14 such that the slot 40 of actuation sled 28 engages flange 42 of actuation channel 44 to enable re-use of the apparatus 10.

It is envisioned that canisters 6 can also be replaced as needed. Alternatively, it is envisioned that reservoirs 4a, 4b can be fluidly coupled to a remote pressure source (not shown), thereby obviating the need for canisters 6. In yet another embodiment, it is envisioned that reservoirs 4a, 4b can be fluidly coupled to a hand actuated pressure source, e.g., a syringe, hand pump, etc.

Although the subject apparatus has been described with respect to preferred embodiments, it will be readily apparent to those having ordinary skill in the art to which it appertains that changes and modifications may be made thereto without departing from the spirit or scope of the subject apparatus. For example, the invention may be applied to endoscopic as well as open-type surgical, e.g., anastomosis, apparatus. The invention may be easily applied to hand-held manually or remotely, e.g., robotically, operated endoscopic linear staplers that employ, e.g., a pair of jaws, e.g., an anvil and a cartridge, for sequentially or simultaneously applying a wound treatment material to a tissue treatment site.

It is further envisioned that reservoirs 4a, 4b may be pressurized when the handle(s) 100 of apparatus 10 are actuated to close and/or otherwise clamp apparatus 10 onto tissue 120. For example, handle(s) 100 of apparatus 10 may act like manual pumps to force additional fluid (e.g., gas or liquid) into reservoirs 4a, 4b thereby increasing the pressure within reservoirs 4a, 4b. Accordingly, when needles 24 penetrate seals 61, 161, the wound treatment material "W" is forced out of reservoirs 4a, 4b.

Figure 10:
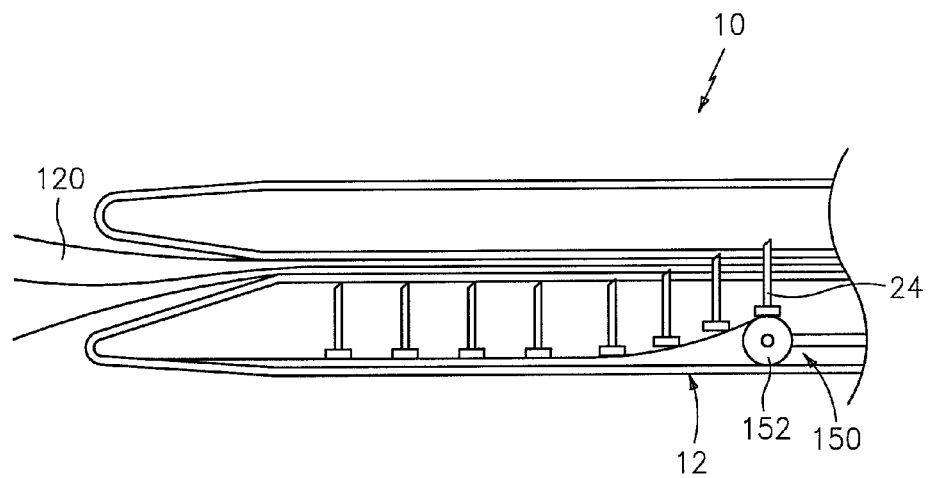
FIG. 10 is a schematic illustration of a distal end of a surgical apparatus including a wound treatment material applicator constructed in accordance with an alternate embodiment of the present disclosure.
Figure 11:
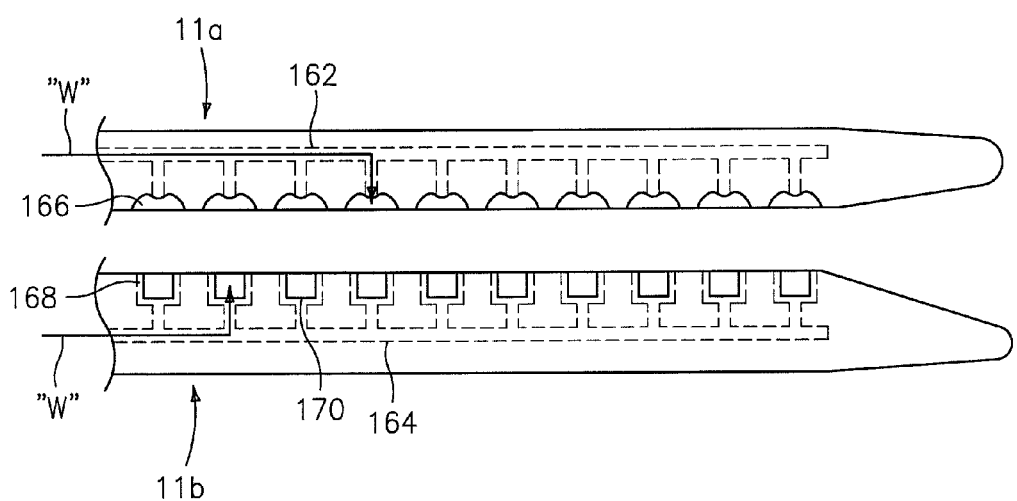
FIG. 11 is a schematic illustration of a distal end of a surgical apparatus including a wound treatment material applicator constructed in accordance with another alternate embodiment of the present disclosure.

Turning now to FIG. 10, in an alternate embodiment, surgical apparatus 10 includes a camming device 150, including a cam roller 152, translatably disposed within body portion 12. In operation, after the distal ends of the first and second-half sections 11a, 11b of surgical apparatus 10 have been clamped onto tissue 120, camming device 150 is advanced distally through body portion 12 and disposable loading unit 20 to deploy needles 24. Desirably, six (6) rows of needles 24 may be provided which extend substantially the entire length of the distal ends of the first and second-half sections 11a, 11b. Once needles 24 have been deployed, wound treatment material "W", in the form of glue and an accelerator may be driven or fed through respective distal ends of the first and second-half sections 11a, 11b and into needles 24 where the two components mix when exiting the perforations formed in needles 24 to join or seal the tissue. Finally, a knife (not shown) may be provided to dissect the tissue into two halves along the middle of the distal ends of the first and second-half sections 11a, 11b. Flow of pressurized fluid and/or of wound treatment material "W" may be activated by signals from one or more suitably situated and activated sensors.

Turning now to FIG. 10, an alternate embodiment of surgical apparatus 10 is shown and described. Surgical apparatus 10 may include a first fluid delivery channel 162 extending through the distal end of the first half-section 11a, and a second fluid delivery channel 164 extending through a distal end of the second half-section 11b. Desirably, first fluid delivery channel 162 is in fluid communication with at least some, preferably, each staple receiving/forming pocket 166 formed in a tissue contacting surface of the distal end of first half-section 11a. Additionally, second fluid delivery channel 164 is in fluid communication with at least some, preferably each staple retaining slot 168 provided in a tissue contacting surface of the distal end of second half-section 11b. A surgical staple 170 is desirably disposed in each staple retaining slot 168. As is conventional, each staple retaining slot 168 is in juxtaposed alignment with each staple receiving/forming pocket 166.

Each channel 162, 164 is fluidly connected to the same or individual fluid sources (not shown), for example as described above. In this manner, fluid in the form of wound treatment material "W" may be delivered to staple retaining slots 168 and/or staple receiving/forming pockets 166 via respective channels 162, 164.

Accordingly, in use, upon firing surgical apparatus 10, staples 170 are deployed from staple retaining slots 168 to penetrate through tissue and to be formed within stapler receiving/forming pockets 166. Concomitantly therewith, wound treatment material "W" is dispensed from staple retaining slots 168 and/or staple receiving/forming pockets 166, as described above.

It will be understood that various modifications may be made to the embodiments of the surgical apparatus disclosed herein. Therefore, the above description should not be construed as limiting, but merely as exemplifications of embodiments. Those skilled in the art will envision other modifications within the scope of the present disclosure.

What is claimed is:

1. A surgical apparatus, comprising:
   a first section and a second section pivotably mounted in relation to the first section for clamping tissue therebetween;
   a cartridge disposed in the second section and having a proximal end and a distal end, the cartridge having a plurality of deployable needles supported within the cartridge, wherein each needle includes a lumen extending therethrough for dispensing a fluid;
   a plurality of pushers disposed in the cartridge, each of the pushers being in operative association with at least one of the needles, wherein the pushers sequentially deploy the needles from the cartridge and into tissue clamped between the first section and the second section upon a firing of the surgical apparatus;
   a reservoir defined in the second section adjacent the pushers of the cartridge, the reservoir containing the fluid; and
   a pressurized canister in fluid communication with the reservoir.

2. The surgical apparatus according to claim 1, wherein the canister is supported on the second section.

3. The surgical apparatus according to claim 1, wherein each pusher includes an opening formed therein allowing the fluid to pass from the reservoir to the respective needle.

4. The surgical apparatus according to claim 1, further comprising an actuation member disposed within the cartridge for translation from the proximal end to the distal end of the cartridge thereby delivering a driving force to each pusher to sequentially deploy the needles from the cartridge.

5. The surgical apparatus according to claim 4, wherein the actuation member comprises a cam roller that translates through the cartridge to interact with the pushers.

6. The surgical apparatus according to claim 4, further comprising a knife blade supported on the actuation member for severing tissue clamped between the first section and the second section, the knife blade traveling along a longitudinal slot provided in the cartridge.

7. The surgical apparatus according to claim 6, wherein a first portion of the needles are disposed on one side of the longitudinal slot and at least a second portion of the needles are disposed on the other side of the longitudinal slot.

8. The surgical apparatus according to claim 1, wherein the fluid is a wound treatment material.

9. The surgical apparatus according to claim 8, wherein the wound treatment material is at least one of an adhesive, a sealant, a hemostat, and a medicament.

10. The surgical apparatus according to claim 1, wherein the first section has a plate including a plurality of needle receiving openings.

11. The surgical apparatus according to claim 10, wherein a distal end of each needle enters a respective needle receiving opening of the first section during actuation of the surgical apparatus.

12. The surgical apparatus according to claim 1, wherein the first section has a first section reservoir, a plurality of needles, and a plurality of pushers, the first section reservoir being in fluid communication with lumens extending through the needles of the first section.

* * * * *